United States Patent
Silvis

(10) Patent No.: US 6,209,385 B1
(45) Date of Patent: Apr. 3, 2001

(54) METHOD AND SYSTEM FOR DETERMINING AIR/FUEL RATIO OF AN ENGINE'S COMBUSTION PROCESS FROM ITS EXHAUST EMISSIONS

(75) Inventor: William M. Silvis, Ann Arbor, MI (US)

(73) Assignee: Horiba Instruments, Inc., Ann Arbor, MI (US)

( * ) Notice: Subject to any disclaimer, the term of this patent is extended or adjusted under 35 U.S.C. 154(b) by 444 days.

(21) Appl. No.: 08/671,516

(22) Filed: Jun. 27, 1996

(51) Int. Cl.[7] .......................... G01M 15/00; F02D 41/14
(52) U.S. Cl. .......................................................... 73/23.32
(58) Field of Search ............................. 73/23.31, 23.32, 73/116, 117.2, 117.3, 118.1, 118.2; 364/431.051, 431.062

(56) References Cited

U.S. PATENT DOCUMENTS

| | | | |
|---|---|---|---|
| 4,751,907 | * | 6/1988 | Yamamoto et al. ................. 73/23.32 |
| 5,231,864 | * | 8/1993 | Ishida et al. ........................ 73/23.32 |
| 5,323,635 | * | 6/1994 | Veno et al. .......................... 73/23.32 |

\* cited by examiner

Primary Examiner—George Dombroske
(74) Attorney, Agent, or Firm—Brooks & Kushman P.C.

(57) ABSTRACT

A computerized method and system are provided for determining air/fuel ratio of an engine's combustion process from its exhaust emissions wherein alternative methods for calculating the amount of water in the exhaust emissions are available according to the measurement situation and/or the preference of the user. The calculation types may include calculation types such as the Brettschneider/Spindt calculation type, the Simons calculation type or the no $O_2$ calculation type. Pop-up menus on a computer monitor are used for selecting the basic calculation type. The algorithm of the present invention preferably uses a fixed point iteration wherein an initial value is assumed for oxygen gas which is then used to calculate water moles and then subsequently the water moles is used to calculate another oxygen value. This is repeated until the new value for oxygen gas is no longer significantly different than the old value for oxygen gas. This happens typically after just a few iterations.

14 Claims, 3 Drawing Sheets

METHOD AND SYSTEM FOR DETERMINING AIR/FUEL RATIO OF AN ENGINE'S COMBUSTION PROCESS FROM ITS EXHAUST EMISSIONS

TECHNICAL FIELD

This invention relates to methods and systems for determining air/fuel ratio of an engine's combustion process and, in particular, to methods and system for determining air/fuel ratio of an engine's combustion process from its exhaust emissions.

BACKGROUND ART

There seem to be an uncountable number of different equations for calculating the air-to-fuel ratio of an engine's combustion process from its exhaust emissions despite the fact that all of the equations are based on the same chemistry and physics of the same combustion phenomena. Authors such as D'Alleva, Spindt, Brettschneider, Lange, Simons, Stivender, Holl and others have published papers that are often referenced as sources for these equations.

D'Alleva wrote the earliest paper regularly cited in the literature. He described the relationship between the exhaust gas composition and the air/fuel ratio. He published charts that could be used to read the A/F ratio based on exhaust concentrations, according the fuel h/c ratio. This was in 1936, before computers and calculators, so such charts were common and necessary in engineering practice.

Eltinge improved on D'Alleva's charts to include incomplete combustion. The charts could also be used without on $O_2$ measurement, but then no estimate of measurement error from the size of a triangle formed on the chart by the intersection of the three measurement lines was available.

Spindt published the next major step forward. He published an actual formula using CO, $CO_2$, HC and $O_2$. It did not require an assumption of complete combustion. Spindt worked for a fuel company, Gulf Oil, so he was sensitive to the fact that combustion was not complete and that the exhaust gas contained a mix of hydrocarbons related in a complicated way to the fuel and the operating mode of the engine.

In 1973, William Holl at AC Spark plug published formulae that did not require a measurement for oxygen. Since the formulae are algebraically complex and he was interested in making real-time calculations at a time when laboratory computers were not so powerful or easy to program, he developed simplified equations by using power series approximations and ignoring the higher order terms. The simpler forms in use today are variations of this idea.

Brettschneider was next in 1979. He added terms to Spindt's equation to account for both water in the ambient air and to incorporate a measured $NO_x$ into the equation, so it no longer needed to be assumed to be 0. He also included terms for oxygenated fuels. He worked for Bosch, so he was sensitive to the importance of A/F for the performance of carburetors and fuel injection systems. His equation is an evolutionary improvement on Spindt and should replace it.

Other investigators such as Piken and Rouf had in the meantime taken Spindt's ideas and developed equations that did not need the $O_2$ measurement. When $O_2$ was present, they proposed using it as validity check. They later extended their result, as did Brettschneider, to include $NO_x$ and $H_2O$.

Next came Simons from the TUEV in 1974. He recognized that the extra degree of freedom provided by an $O_2$ measurement could be used to calculate the equilibrium constant K instead of as a validity check on the other measurements. This improved the agreement of his formula to measured test data. It showed that K could vary widely, and that it was generally lower than the 3.5 that was commonly assumed.

Recently, Mitsubishi investigators Fukui, Tamura, Omori, Saitoh, apparently unaware of the work of Brettschneider and Simons, improved on the Spindt formula by including NO and water vapor. More significantly, they also noted that the equilibrium constant seemed to be modified by the action of the catalyst. They recommended only using the engine gasses for determining A/F. The Simons equation may have performed better with post catalyst measurements, but they did not investigate it.

The equations noted above can be somewhat complex. There are a number of assumptions that are made of the values of physical constants, some chooices about how to use the information that is available, and there is a good deal of flexibility in the algebraic forms that are used to represent the equation.

The physical constants are generally well known, but not precisely known. A slightly different value, when taken into a formula and used in algebraic reformations to calculate other constants, results in formulas with different coefficients. Everyone can recognize that 20.95 and 20.9 are just two slightly different values for the assumed concentration of oxygen in air. But when this number is used to get mole proportions between nitrogen and oxygen, it is not so easy to recognize that 4.77418 and 3.7733 are both. derived from this same physical constant. It is also apparent that the constants are used with varying numbers of significant digits.

Most of the differences between equations are a matter of algebra. Since many expressions arise during the derivation of the A/F equation, there is much room for creativity in the selection of the algebraic steps taken in the simplification process and in the final form of the simplified result.

The very same equation can be expressed using algebraic forms that are so different they can no longer be recognized as equivalent.

Another source of differences are the basic assumptions about what will be significant to include in the calculation. For example:

It is important to include the humidity of the ambient air?
Is there significant water in the fuel itself?
Can the contribution of $NO_x$ be ignored?
Can it be assumed that all the $NO_x$ is NO?
What is the number of carbon atoms on a molecule of HC in the exhaust? Is it the same as in the fuel?
What is the water/gas equilibrium constant?3.8, 3.5, 3.2, or much smaller?
Can it be assumed that the cooler dries the sample completely?

Theoretically, if combustion is complete (HC=0), if $NO_x$ can be neglected, and if the water/gas equilibrium is assumed, a measurement of just CO2 and CO are enough to determine the air/fuel ratio.

If combustion is not complete, one can add a measurement of HC and an assumption about how many molecules of C are in an HC molecule in the exhaust gas. The hydrocarbon molecules are generally smaller in the exhaust than they are in the fuel (except for CNG). Today, combustion is often nearly complete, so under commonly accepted assumptions and for fair accuracy, it is only necessary to measure CO, CO2 and HC.

To be more accurate, a measurement of $NO_x$ and an assumption about how much was NO and how much $NO_2$ can be applied. Usually, it is assumed $NO_2=0$. This may be undesirable for diesel vehicles, but the effect of $NO_x$ on the result is small in any case.

With these measurements of HC, CO, $CO_2$ and $NO_x$, the formulae vary only as to whether they include terms for water in the ambient air and fuel, and what values they assume for fundamental constants.

Another dimension opens up however, when a measurement of $O_2$ is available. This measurement provides another degree of freedom. The degree of freedom can be used in a number of ways. It can eliminate the need for one of the basic assumptions, or it can be used as an error check on the accuracy and consistency of the other measurements. The Simons' method uses it to eliminate the need to assume a value for the water-gas equilibrium constant K. This is perhaps the most practical use.

In determining A/F, equations are usually set up for a fixed measuring configuration, where the values. to be measured and the assumptions to be made are known well ahead of time and are not expected to change. However, a given measurement system often must adapt itself to different situations, depending on customer preference and available measurements. Therefore, rather than a single equation calculation type, it is desirable to have a measurement system that includes an algorithm which calculates the air/fuel ratio under these different circumstances.

SUMMARY OF THE INVENTION

An object of the present invention is to provide a method and system for determining air/fuel ratio of an engine's combustion process from its exhaust emissions wherein alternative methods are available according to the measurement situation or the preference of the user.

In carrying out the above object and other objects of the present invention, a method is provided for determining air/fuel ratio of an engine's combustion process from its exhaust emissions. The method includes the steps of taking a sample of the exhaust emissions from an operating engine to obtain exhaust gases and water, measuring concentration of the exhaust gases in the sample and providing corresponding exhaust gas concentration data and selecting a calculation type from a predetermined set of calculation types. The method also includes the steps of calculating an amount of water produced in the combustion process based on the selected calculation type and the exhaust gas concentration data and calculating an amount of oxygen used in the combustion process based on the amount of water produced in the combustion process and the exhaust gas concentration data. Finally, the method includes the steps of calculating the air/fuel ratio based on the calculated amount of oxygen and displaying the air/fuel ratio.

Preferably, the method also includes the step of providing initial oxygen and water values for an amount of oxygen used in the combustion process and the amount of water produced in the combustion- process, respectively.

Also, preferably, the method includes the steps of calculating intermediate values for the water and the oxygen and then comparing the intermediate oxygen value with the initial oxygen value to obtain a difference value which, if less than a predetermined amount, becomes a final oxygen value. The step of calculating the air/fuel ratio is based on this final oxygen value.

Still further, preferably, the set of calculation types includes Brettschneider calculation type and a Simons calculation type.

Systems are also provided for carrying out the above methods.

The above objects and other objects, features, and advantages of the present invention are readily apparent from the following detailed description of the best mode for carrying out the invention when taken in connection with the accompanying drawings.

BEST MODE FOR CARRYING OUT THE INVENTION

Figure 1:
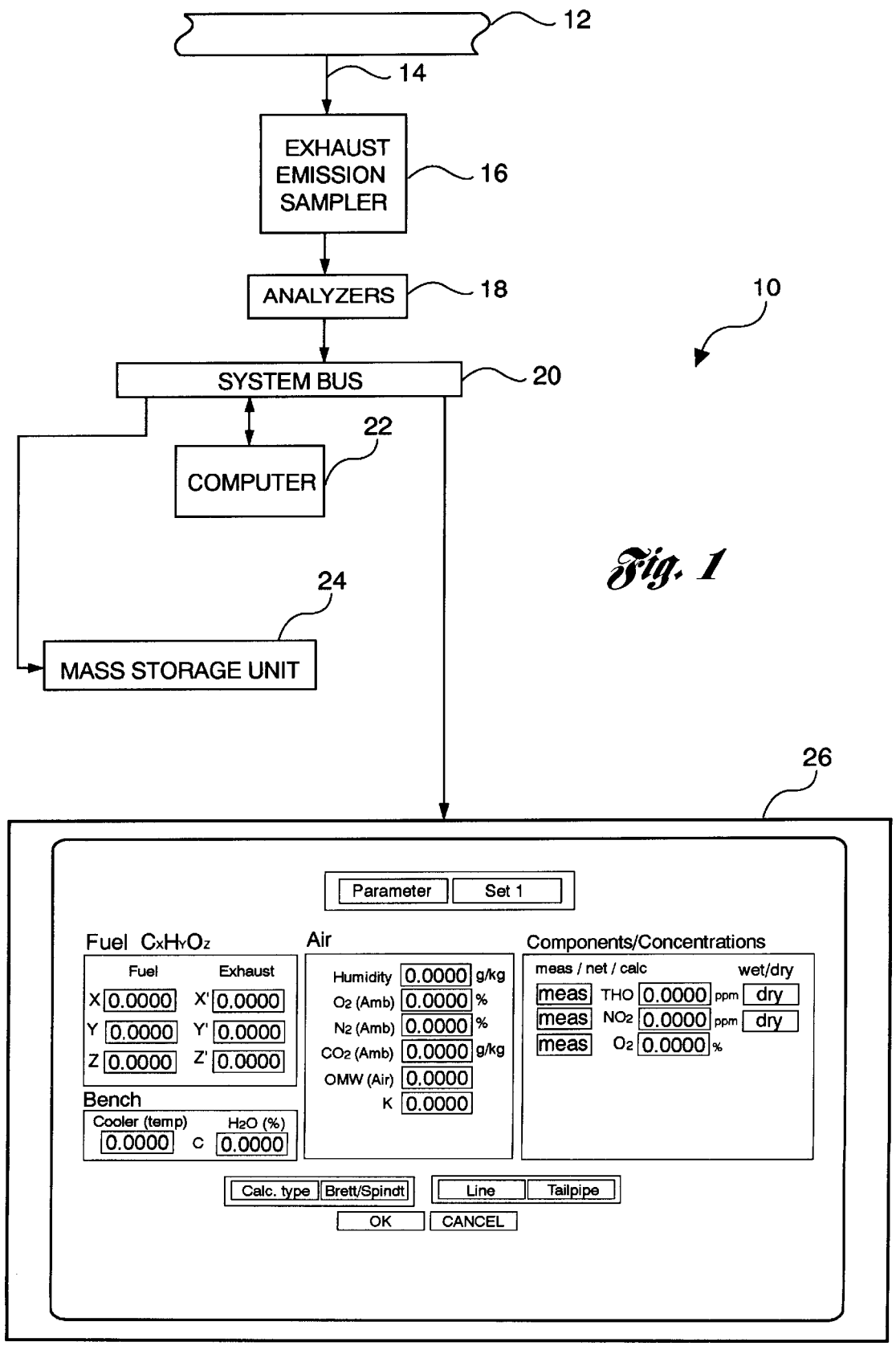
FIG. 1 is a schematic view of a system for calculating air/fuel ratio of an engine's combustion process from its exhaust emissions.

Referring now to the drawing Figures, and in particular to FIG. 1, there is illustrated a system, generally indicated at 10, for determining air/fuel ratio of an engine's combustion process from its exhaust emissions. Exhaust from an exhaust pipe 12 fluidly coupled to an operating engine (not shown) and by a tailpipe adapter 14 to an exhaust emission sampler 16 In general, the exhaust emission sampler 16 prepares a sample such as a diluted sample of exhaust gas for analysis by exhaust emission analyzers 18 for analyzing the sample. The sampler 16 measures the concentration of exhaust substances (i.e. emissions of, for example, Co, $CO_2$, hydrocarbons (HC), $NO_x$, $SO_x$, and the like) contained in the exhaust gas of an engine such as the engine of an automotive vehicle.

Typically, in order to measure the concentration of exhaust gas components directly, analysis must either be done at elevated temperatures in specially designed instrumentation or the water, which condenses when the exhaust gases cool, must be removed before-analysis.

The analyzers 18 typically measure concentration of the exhaust gases in the sample and provide corresponding exhaust gas concentration data to a system bus 20, which may be a standard bus, which allows intersystem communication such as to a computer 22, a mass storage unit 24, and a monitor 26.

The computer 22 may be a PC having a sufficient amount of RAM and hard disk space for performing the algorithms associated with the present invention.

The system of the present invention may be programmed at the mass storage unit 24 to include a predetermined set of calculation types as described hereinbelow.

Referring specifically to a touch screen of the monitor 26, there is described in graphic form therein, and as described hereinbelow, how an air/fuel ratio set function allows one to set and select the type of calculation used for air/fuel determination. A parameter menu provides one with four variable settings. One can select and edit each set and the changes are saved. This allows one to create four different parameter sets that can be quickly recalled. Whenever changes are made to parameter variables, the parameter set is saved in the new form.

The panel of the monitor 26 offers one ease and flexibility in selecting and editing AFR calculations. To set variables, one presses numbers, toggle switches or pop-up menus. There are four main areas for entering data and two pop-up menus.

The data entry areas are for fuel, air, concentrations and bench features. In the fuel data entry area, one can type in the x, y and z values for the fuel being used. This area includes entry windows for the standing fuel and exhaust.

The air data entry area allows one to enter the values for humidity, ambient $O_2$, $N_2$ and $CO_2$, as well as the gram molecular weight of air and the K value.

The concentration data entry area contains the various analyzer components that are used in the calculation. The components displayed depend on the type of calculation being used. The full complement of components is THC, $NO_x$, and $O_2$. For each component, one can use the concentration measured by the system analyzers or one can enter a fixed value. To use the measured concentration, press the toggle button until it reads "meas". If one wants to use a fixed value, press the toggle button until it reads "set". When the button reads "set", the concentration appears in yellow numbers. Press the number to edit. For THC and $NO_x$, if the system contains both types of analyzers, one may choose to use hot or cold analyzers. Cold analyzer only read gas that has passed through a chiller to remove the excess water. To select cold analyzers, select "dry" from the wet/dry toggle. For heated analyzers, select the "wet" option. If the system does not contain one type of analyzer, the corresponding toggle button does not function.

The pop-up menus are for selecting the basic. calculation type and the desired line. The calculation types include Brettschneider/Spindt, No $O_2$, Simons and Custom. By selecting one of these options, the panel automatically adapts to certain parameters of the selected calculation type. For Brettschneider/Spindt, the calculation uses the measured value for $O_2$ and an assumed value for the water/gas equilibrium, K. The No $O_2$ calculation option is for cases where $O_2$ is not measured. This calculation type estimates the oxygen concentration that must be present in order to calculate the air/fuel ratio. The Simons option uses the measured concentration for oxygen, but does not assume a value for K. This calculation is useful for post catalyst measurements, where the K value may be altered by the catalyst. The custom option offers a mode for presenting one's own calculation requirements.

Detailed Description of Algorithm to Calculate Air/Fuel

First consider the equation for ideal complete combustion. This is the basis for computing the stoichiometric amount of oxygen (or air) that is used to burn a given fuel. This quantity is used to calculate the normalized air/fuel ratio, lambda (or phi, the inverse of lambda), and this equation is a good start toward a practical chemical equation to describe actual combustion:

$$C_xH_yO_z + O_2 \rightarrow CO_2 + H_2O$$

If one balances the mole quantities of the carbon, hydrogen and oxygen in this reaction, the balanced equation is written:

$$C_xH_yO_z + \left(x + \frac{y}{4} - \frac{z}{2}\right)O_2 \rightarrow xCO_2 + \frac{y}{2}H_2O$$

So one can see that when the combustion is complete, and the mixture of reactants is stoichiometric, the moles of oxygen required are:

$$n_{stoich} = x + \frac{y}{4} - \frac{z}{2}$$

Actual combustion and the resulting exhaust gas composition can be modeled quite well when one modifies this equation to account for non-ideal circumstances.

The first of the non-ideal circumstances is the actual composition of the combustion air. It is often assumed that air is a simple mixture of oxygen and nitrogen. Actually, air contains other gases in measurable amounts. There is about 1.8% Argon and 0.035% $CO_2$ in air. The inert gases do not take part in the combustion and can be lumped together with the $N_2$ that does not react. The $CO_2$ present is small, ignoring it causes a 0.2% error. For an equation to represent the combustion of idealized dry air and fuel, one uses the following (assuming the concentration of oxygen in air is 20.95%):

$$C_xH_yO_z + \left(x + \frac{y}{4} - \frac{z}{2}\right)(O_2 + 3.7733N_2) \rightarrow$$
$$xCO_2 + \frac{y}{2}H_2O + \left(x + \frac{y}{4} - \frac{z}{2}\right)3.7733N_2$$

For the general case of an actual combustion, there may be more or less moles of oxygen (air) than the stoichiometric amount. In this case, the factor lambda, the excess oxygen factor or normalized air/fuel ratio, is used to describe the combustion chemistry. It is the ratio of the moles of oxygen actually used to the stoichiometric amount:

$$\lambda = \frac{n}{n_{stoich}} = \frac{n}{\left(x + \frac{y}{4} - \frac{z}{2}\right)} \quad (1)$$

The mass air/fuel ratio, which is also sometimes still used, even though its value depends on the type of fuel, can be calculated from lambda in a simple way:

$$AF = \frac{28.97}{(x \cdot 12.011 + y \cdot 1.008 + z \cdot 15.9994)} \cdot \frac{1}{[O_2]_{amb}} \cdot \left(x + \frac{y}{4} - \frac{z}{2}\right) \cdot \lambda \quad (2)$$

It is clear then, that to calculate air/fuel ratios from actual, measured exhaust gas concentrations, one needs to calculate n, the amount of oxygen actually used in the combustion. To do this, one needs a more practical chemical equation for the combustion, one that also accounts for the following shortcomings of the idealized equation shown above.

1. There is usually about one percent of water in ambient air. This water can affect the combustion by changing the peak temperature in the combustion chamber and by affecting the equilibrium concentrations in the water-gas equilibrium between $CO_2$, CO, $H_2O$ and $H_2$ (details below). The Brettschneider equation includes terms for water and a study by Mitsubishi observed and measured the effect. If a measurement of the water in the air is available as absolute humidity (g/kg dry air), one notes that: (the physical constants for air are taken from Heywood, p. 65):

$$H_{abs} = \frac{n_{H_2O} \cdot 18.016}{n_{air} \cdot 28.962} \cdot 10^3$$

$$C = \frac{1.6076 \cdot 10^{-3}}{[O_2]_{amb}}$$

$$\frac{n_{H_2O}}{n_{O_2}} = C \cdot H_{abs}$$

2. At combustion temperatures, and especially if there is a lack of sufficient oxygen, the $CO_2$ and $H_2O$ dissociate and produce some CO and some $H_2$.
3. Not all of the fuel is burned. Some of it appears in altered form as hydrocarbons in the exhaust. Also, when the mixture is lean, there is excess $O_2$ in the exhaust.

4. Some of the nitrogen from the ambient air reacts at the high temperature and pressures in the combustion chamber to form NO and $NO_2$. These reactions heavily favor the production of NO. In emissions measurement, one commonly measure both and represent the value as $NO_x$. The same is done here, and it is assumed that the result behaves chemically as NO.

5. There is some $CO_2$ already in the air. This has a very small effect (0.2%) on calculated results, but since it is reasonably well known, it can be accounted for. Also, it is useful to parameterize the composition of the air. There are usually small differences in the proportions of $O_2$, $N_2$ and $CO_2$ in the combustion air that different investigators use. It may be better to incorporate them as parameters to accommodate these differences, rather than to lose their identity by combining them with other constants in the equations. To do this, one introduces the following air composition factors:

$$A = \frac{[N_2]_{amb}}{[O_2]_{amb}} \approx 3.774$$

$$B = \frac{[CO_2]_{amb}}{[O_2]_{amb}} \approx 0.16$$

6. Concentrations are often measured on a dry basis, after the water has been removed from the sample in a cooler or heat exchanger. However, not all of the water is removed. A small correction based on the temperature of the cooler is needed.

An unbalanced chemical equation for this combustion that includes terms for the above-mentioned issues is:

$$C_xH_yO_z + n(O_2 + A \cdot N_2 + B \cdot CO_2 + C \cdot H_{abs} \cdot H_2O) \rightarrow aCO_2 + bCO + cH_2 + dH_2O + eO_2 + fN_2 + gNO_x + hC_x, H_y, O_z$$

To be able to calculate n, one obtains a set of equations for the unknown mole quantities by balancing this equation. We write 5 equations; the 4 atomic balances (C, H, O, N) and the total mole balance.

Carbon balance:

$$x + n \cdot B = a + b + x^1 \cdot h \quad (3)$$

Hydrogen balance:

$$2 \cdot n \cdot C \cdot H_{abs} + y = 2 \cdot c + 2 \cdot d + y^1 \cdot h \quad (4)$$

Oxygen balance:

$$z + 2n + 2n \cdot B + n \cdot C \cdot H_{abs} = 2a + b + d + 2e + g + z^1 \cdot h \quad (5)$$

Nitrogen balance:

$$2 \cdot n \cdot A = 2f + g \quad (6)$$

Total moles (dry) balance:

$$n_{tot} = a + b + c + e + f + g + h \quad (7)$$

One normally measures the concentrations of HC, CO, $CO_2$ and $NO_x$. Concentrations are mole fractions. They are usually measured on a dry basis, that is, after most water has been removed from the sample. They can be related to the mole quantities by the following relation, ($n_{H2Ocooler}$ is the moles of water left in the sample after it exits the cooler).

$$[X] = \frac{n_x}{n_{tot} + n_{H20_{cooler}}}$$

To compensate for the water left after the gas exits the cooler, one can use the vapor pressure of water at the cooler temperature. This gives:

$$[H_2O]_{cooler} = \frac{P_{vap}(T_{cooler})}{T_{baro}} = \frac{n_{H_2O_{cooler}}}{n_{tot} + n_{H_2O_{cooler}}}$$

So for example in the case of $CO_2$, $$a = [CO_2] \cdot (n_{tot} + n_{H20_{cooler}}) \quad (8)$$

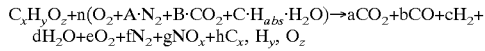

One adopts the convention that [HC] is always the total hydrocarbon concentration, as measured by a FID, so that for this component:

$$h = [HC] \cdot (n_{tot} + n_{H20cooler})/x^1$$

If the HC is measured dry, one can apply the cooler correction term as above. If it is measured wet, with a heated instrument, then we must include the moles of water in the exhaust instead:

$$h = [HC] \cdot (n_{tot} + d)/x^1 \quad (9)$$

Since the first equation above includes only known parameters and mole quantities whose concentrations are always measured, CO2, CO and HC, it can be used to calculate $n_{tot}$:

$$x + B \cdot n = ([CO_2] + [CO] + [HC]) \cdot (n_{tot} + n_{H20_{cooler}}) \quad (10)$$

$$n_{tot} = \frac{x + B \cdot n}{[CO_2] + [CO] + [HC]} \cdot (1 - [H_2O]_{cooler})$$

There are now the four unknowns, n, c, d, and f, and the remaining 4 equations.

The oxygen balance provides a convenient solution for n:

$$n = \frac{2a + b + d + 2e + g + z'h - z}{2 + 2 \cdot B + C \cdot H_{abs}} \quad (11)$$

At this point, one only needs to develop an expression for d, the moles of water, in order to solve for n and therefore lambda. It is also at this point that the methods of Spindt and Brettschneider differ from the methods of Simons. The differences in these approaches can be viewed simply as a difference in the technique used to calculate d. Brettschneider and Spindt use another chemical reaction, the water/gas reaction, and Simons uses the remaining two equations, the nitrogen balance and the total moles balance.

At the high temperature and pressures in the exhaust cylinder during the combustion of a rich mixture of air and fuel, the $CO_2$ and $H_2O$ in the mixture dissociate, creating some $H_2$ and some CO. This is described by the following chemical equation for the water/gas reaction. These species reach an equilibrium described by the equilibrium constant for this reaction, K. The equilibrium depends on the combustion temperature. As the gases cool down as they leave the cylinder, the proportions are frozen at the equilibrium concentrations.

$$CO_2 + H_2 \rightarrow CO + H_2O$$

The equilibrium is described by:

$$K = \frac{b \cdot d}{a \cdot c} \quad (11)$$

The value depends on the combustion temperature. For 1700 K, the theoretical value is 3.388. Values of 3.5 and 3.8 are described in the literature as producing good matches between this theory and observations. The action of a catalyst has been observed to change the effective value for K as well. This is not surprising, since the catalyst causes the combustion to continue at a lower temperature and converts the CO into $CO_2$.

Next, from the hydrogen balance, one can get an expression for the hydrogen moles, c:

$$c = \frac{y - h'h}{2} + n \cdot C \cdot H_{abs} - d \quad (12)$$

Substituting this into the equilibrium condition, one gets the following expression for the moles of water:

$$d = \frac{y + 2 \cdot n \cdot C \cdot H_{abs} - y'h}{2\left(\frac{b}{a \cdot K} + 1\right)} \quad (13)$$

Another approach is described by Simons. This method uses the nitrogen and mole balance to find d. From the nitrogen balance:

$$f = n \cdot A - g/2$$

Substituting this into the mole balance:

$$n_{tot} = a + b + c + e + n \cdot A - \frac{g}{2} + g + h$$

Next, substitute the expression for n from the oxygen balance, and rearrange terms:

$$d = \left(n_{tot} - a - b - c - e + \frac{g}{2} - g - h\right) \cdot \frac{2 + 2 \cdot B + C \cdot H}{A} - \\ 2a - b - 2e - g - z'h + z \quad (14)$$

One can substitute the Expression 12 for hydrogen moles and get the following algebraic simplification:

$$d = \frac{\left(n_{tot} - a - b - \left(\frac{y - h'h}{2} + n \cdot C \cdot H_{abs}\right) - e - \frac{g}{2} - h\right) \cdot \frac{2 + 2 \cdot B + C \cdot H_{abs}}{A} - 2a - b - 2e - g - z'h + z}{1 - \frac{2 + 2 \cdot B + C \cdot H_{abs}}{A}}$$

If d is known from the water gas equilibrium, similar steps can be used to calculate e, the oxygen concentration, instead. This is useful for cases when the oxygen concentration is not measured. This is the idea behind the third type of A/F calculation, the Piken and Rouf type.

$$e = \frac{n_{tot} - a - b - c - \frac{A}{(2 + 2B + C \cdot H_{abs})} \cdot}{1 + \frac{2A}{2 + 2B + C \cdot H_{abs}}} \quad (15)$$

$$\frac{(2a + b + d + 2e + g + z'h - z) + \frac{g}{2} - g - h}{1 + \frac{2A}{2 + 2B + C \cdot H_{abs}}}$$

If both e and d are already available from measurement, and if one assumes a constant for the water gas equilibrium, (Brettschneider/Spindt type methods), then one can use the nitrogen and mole balance equations to calculate a quality number. It is most natural to calculate the actual $O_2$ concentration (relative to dry air) of the ambient air used for combustion.

From the nitrogen balance:

$$n_{N_2 amb} = f + \frac{g}{2}$$

Substitute this into the mole balance:

$$n_{N_2 amb} = n_{tot} - a - b - c - e - g - h + \frac{g}{2}$$

From this, one calculates the concentration of oxygen in the ambient air:

$$[O_2] = \frac{n}{n + n_{N_2 amb} + n_{CO_2 amb}} \quad (16)$$

$$= \frac{n \cdot (1 - [CO_2]_{amb})}{n + n_{N_2 amb}}$$

This should be a constant equal to the assumed value of the ambient oxygen concentration. If it differs from this, it is an indication of a measurement error. It can also be used to verify proper time alignment of the measured values. It should not change even if the vehicle is accelerated and decelerated through the driving cycle.

At this point, it is important to make two remarks about the calculations outlined in the above equations. First, the several equations above could be shortened and combined into one larger equation. This was often done in the past when these methods had to be prepared for tedious hand calculation. However, this is hardly necessary today when high performance computers are on desktops or in pockets and convenient spread-sheets perform the calculations. The algebra of the simplification process is error prone and hides the physical interpretations of the terms.

Secondly, the equations above are circular. The calculation for n depends on d, which in turn depends on n. The circularity arises when some of the smaller effects that are usually ignored are included. Of course, this could be resolved by a great deal of algebra and a very complicated closed form equation for n could be written. However, this is not necessary. It is much easier to use a fixed point iteration. An initial value for n is assumed and is used to calculate d and subsequently another n. This is repeated until the new values for n no longer are significantly different. This typically happens after just a few iterations.

Figure 2A:
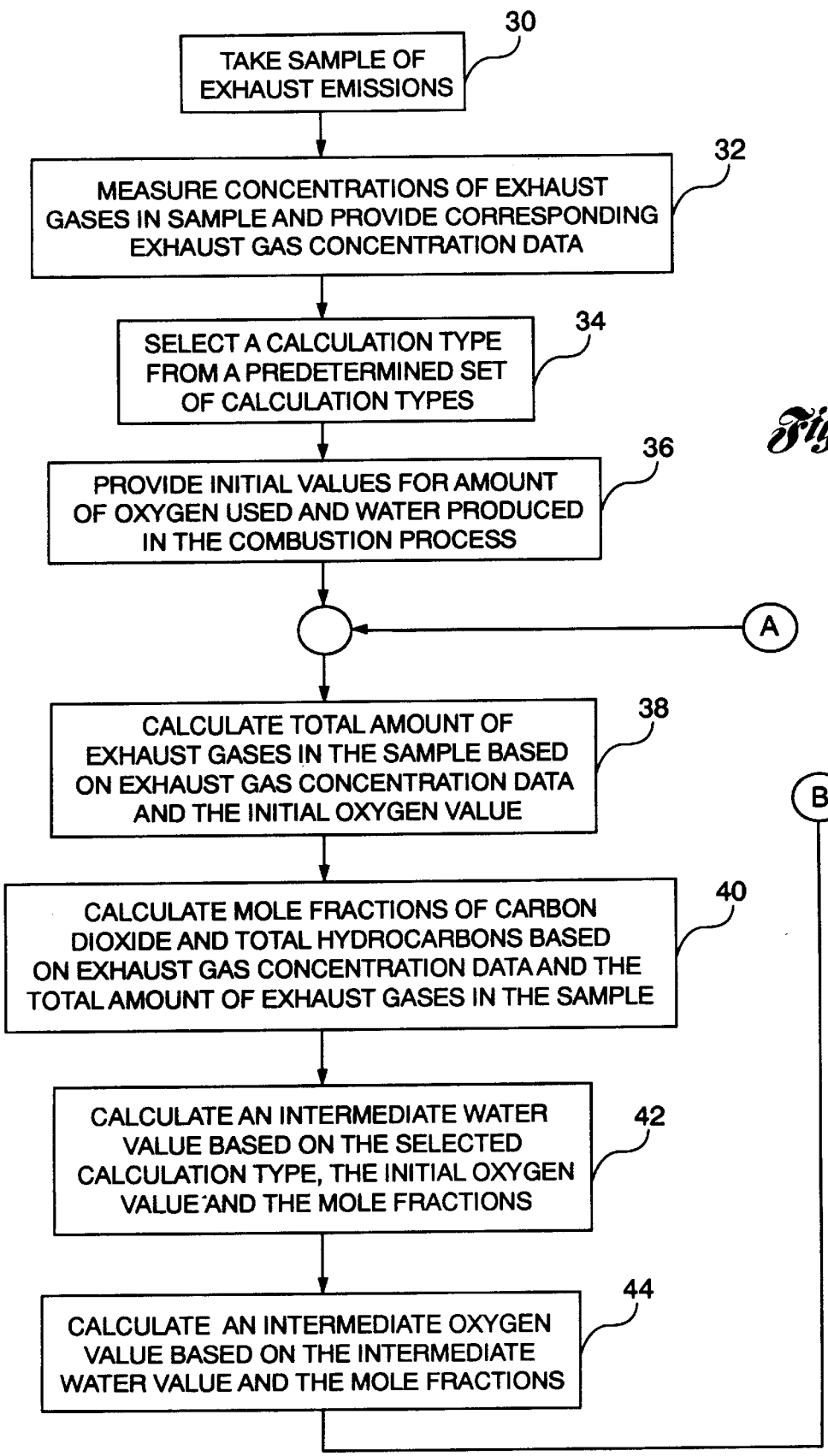
FIGS. 2a and 2b show a block diagram flow chart illustrating a method for calculating air/fuel ratio of an engine's combustion process from its exhaust emissions.
Figure 2B:
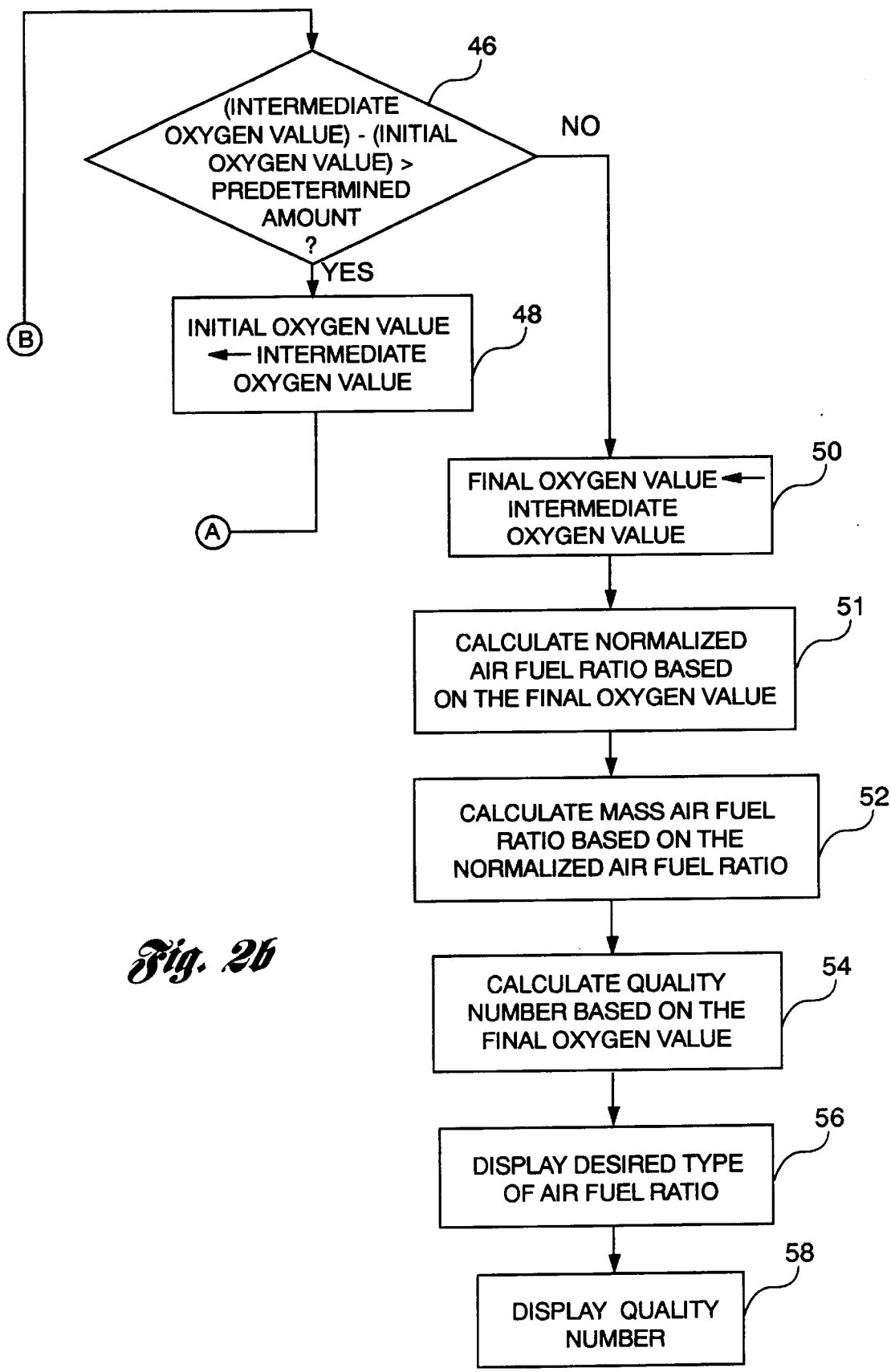

Referring now to FIG. 2, there is illustrated in block diagram flow chart form, the algorithm for calculating air/fuel ratio from exhaust emissions.

Initially, whenever HC or $NO_x$ are not available, the user applies a user-supplied default or zero for the concentration.

At block 30, examples are taken of the exhaust emissions such as by the exhaust emission sampler 16.

At block 32, concentrations of the exhaust gases in the sample are measured and corresponding exhaust gas concentration data is provided such as by the analyzers 18.

At block 36, initial values are provided for the amounts of oxygen used and water produced in the combustion process.

At block 38, the total amounts of the exhaust gases in the sample are calculated based on the exhaust gas concentration data and the initial oxygen value as indicated by Equation 10 noted above.

At block 40, mole fractions of carbon dioxide and total hydrocarbons are calculated based on the exhaust gas concentration data and the total amount of exhaust gases in the sample per Equations 8 and 9.

At block 42, an intermediate water value based on the selected calculation type is calculated, the initial oxygen value and the mole fractions. The selected calculation type may be the Brettschneider K formula of Equation 13. If an oxygen measurement is not available, the water moles calculated from this equation is used to calculate by way of Equation 15.

Alternatively, water moles can be calculated from the Simon's formula of Equation 14 after calculating c from Equation 12.

At block 44, an intermediate oxygen value is calculated based on the intermediate water value and the mole fractions, as indicated by Equation 11.

At block 46, an intermediate oxygen value is subtracted from the initial oxygen value and the difference is compared to a predetermined amount. If the difference is greater than the predetermined amount, block 38 is re-entered after first making the initial oxygen value equal to the intermediate oxygen value as indicated at block 48.

If the difference is relatively small (i.e. is less than or equal to the predetermined amount), block 50 is entered wherein the intermediate oxygen value is determined to be the final oxygen value.

At block 51, normalized air/fuel ratio, $\lambda$, is calculated based on the final oxygen value per Equation 1.

If mass air/fuel ratio is desired, it is calculated at block 52 based on the normalized air/fuel ratio previously calculated at block 51 in accordance with Equation 2.

At block 54, a quality number based on the final oxygen value is calculated according to Equation 16.

At block 56, the desired type of air/fuel ratio is displayed on the monitor 26.

At block 58, the quality number is displayed on the monitor 26.

Alternatively, the algorithm can be expressed by the following numbered statements:

1. Assume an initial value of 1.0 for n, and an initial value of 1.0 for d.
2. Calculate $n_{tot}$ from HC, CO, and $CO_2$ concentrations according to Equation 10. Calculate the mole fractions from the concentrations and $n_{tot}$ per Equations 8 and 9.
3. Calculate the water moles, d, from one of:
   The Brettschneider K formula, Equation 13. If an oxygen measurement is not available, use this d and calculate e by Equation 15 or
   Calculate c from Equation 12. Then calculate d from the Simons formula, Equation 14.
   or
   An assumed fixed value.
5. Calculate n from the total oxygen moles, Equation 11.
6. Compare this to the old value for n. If the difference is small, go to the next step. Otherwise, go back and repeat, starting with the $n_{tot}$ calculation, step 2.
7. Once n is calculated, calculate lambda from $n/n_{O2}$, Equation 1.
8. If the mass ratio is desired, calculate it according to Equation 2.
9. Calculate the quality number according to Equation 16.

The following specific calculation types are contemplated by the method and system of the present invention.

Brettschneiter/Spindt

Uses the measured oxygen and an assumed value for the water/gas equilibrium constant, K. One of the older and most commonly used formulae. In addition to the A/F, a quality number can be calculated to gauge the size of any measurement error.

NO $O_2$

Used when the $O_2$ is not measured. It estimates the $O_2$ which must have been present in order to calculate the A/F.

Simons

Uses a measured oxygen, but does not assume a value for the equilibrium constant, K. Useful for post catalyst measurements, where the K value is not well known and may have been changed by the catalyst.

While the best mode for carrying out the invention has been described in detail, those familiar with the art to which this invention relates will recognize various alternative designs and embodiments for practicing the invention as defined by the following claims.

What is claimed is:

1. A computer-implemented method for determining air/fuel ratio of an engine's combustion process from its exhaust emissions, the method comprising the steps of:
   taking a sample of the exhaust emissions from an operating engine to obtain exhaust gases and water;
   measuring concentration of the exhaust gases in the sample, and providing corresponding exhaust gas concentration data;
   selecting a calculation type from a predetermined set of calculation types stored in a computer system, including a computer;
   calculating with the computer an amount of water produced in the combustion process based on the selected calculation type and the exhaust concentration data;
   calculating with the computer an amount of oxygen used in the combustion process based on the amount of water produced in the combustion process and the exhaust gas concentration data;
   calculating with the computer the air/fuel ratio based on the calculated amount of oxygen; and
   displaying the air/fuel ratio on a display coupled to the computer.

2. The method of claim 1 wherein the sample of exhaust emissions includes oxygen gas and wherein the method further comprises the steps of measuring concentration of the oxygen gas in the sample and providing corresponding oxygen gas concentration data.

3. The method of claim 2 wherein the set of calculation types includes a Brettschneider calculation type which utilizes the oxygen gas concentration data.

4. The method of claim 2 wherein the set of calculation types includes a Simons calculation type which utilizes the oxygen gas concentration data.

5. The method of claim 1 wherein the set of calculation types includes a no $O_2$ calculation type.

6. The method of claim 1 further comprising the step of removing water from the sample after the step of taking the sample and before the step of measuring the concentration of exhaust gases.

7. A computer-implemented method of determining air/fuel ratio of an engine's combustion process from its exhaust emissions, the method comprising:
- a) taking a sample of the exhaust emissions from an operating engine to obtain exhaust gases and water;
- b) measuring concentration of the exhaust gases in the sample, and providing corresponding exhaust gas concentration data;
- c) selecting a calculation type from a predetermined set of calculation types stored in a computer system including a computer;
- d) providing to the computer system initial oxygen and water values for amount of oxygen used in the combustion process and amount of water produced in the combustion process, respectively;
- e) calculating with the computer exhaust gas concentrations based on the exhaust gas concentration data and the initial oxygen value;
- f) calculating with the computer an intermediate water value based on the selected calculation type, the initial oxygen value, and the exhaust gas concentrations;
- g) calculating with the computer an intermediate oxygen value based on the intermediate water value;
- h) comparing with the computer the intermediate oxygen value with the initial oxygen value to obtain a difference value;
- i) repeating steps e) through h) and changing the initial oxygen value to be the intermediate oxygen value if the difference value is greater than a predetermined amount;
- j) determining with the computer the intermediate oxygen value to be a final oxygen value if the difference value is within the predetermined amount; and
- k) calculating with the computer the air/fuel ratio based on the final oxygen value.

8. A system for determining air/fuel ratio of an engine's combustion process from its exhaust emissions, the system comprising:
- a sampler for taking a sample of the exhaust emissions from an operating engine to obtain exhaust gases and water;
- analyzers for measuring concentration of the exhaust gases in the sample, and providing corresponding exhaust gas concentration data;
- means for selecting a calculation type from a predetermined set of calculation types;
- means for calculating an amount of water produced in the combustion process based on the selected calculation type and the exhaust gas concentration data;
- means for calculating an amount of oxygen used in the combustion process based on the amount of water produced in the combustion process and the exhaust gas concentration data;
- means for calculating the air/fuel ratio based on the calculated amount of oxygen; and
- means for displaying the air/fuel ratio.

9. The system and claimed in claim 8 wherein the sample of exhaust emissions includes oxygen gas and wherein the system further includes an analyzer for measuring concentration of the oxygen gas in the sample and providing corresponding oxygen gas concentration data.

10. The system as claimed in claim 9 wherein the set of calculation types includes a Brettschneider calculation type which utilizes the oxygen gas concentration data.

11. The method of claim 9 wherein the set of calculation types includes a Simons calculation type which utilizes the oxygen gas concentration data.

12. The method of claim 8 wherein the set of calculation types includes a no $O_2$ calculation type.

13. The system as claimed in claim 7 further comprising means for removing water from the sample.

14. A system for determining for determining air/fuel ratio of an engine's combustion process from its exhaust emissions, the system comprising:
- a sampler for taking a sample of the exhaust emissions from an operating engine to obtain exhaust gases and water;
- analyzers for measuring concentration of the exhaust gases in the sample, and providing corresponding exhaust gas concentration data;
- means for selecting a calculation type from a predetermined set of calculation types;
- means for providing initial oxygen and water values for an amount of oxygen used in the combustion process and an amount of water produced in the combustion process, respectively;
- means for calculating exhaust gas concentrations based on the exhaust gas concentration data and the initial oxygen value;
- means for calculating an intermediate water value based on the selected calculation type, the initial oxygen value and the exhaust gas concentrations;
- means for calculating an intermediate oxygen value based on the intermediate water value;
- means for comparing the intermediate oxygen value with the initial oxygen value to obtain a difference value;
- means for changing the initial oxygen value to be the intermediate oxygen value if the difference value is greater than a predetermined amount;
- means for determining the intermediate oxygen value to be a final oxygen value is the difference value is within the predetermined amount; and
- means for calculating the air/fuel ratio based on the final oxygen value.

* * * * *